(12) United States Patent
Scherf et al.

(10) Patent No.: US 8,514,387 B2
(45) Date of Patent: Aug. 20, 2013

(54) ARRANGEMENT FOR MEASURING SECTIONS OF TRACK FOR THE PURPOSE OF MAINTAINING RAILROAD TRACKS

(76) Inventors: Wilfried Scherf, Hummelshain (DE); Michael Luddeneit, Hummelshain (DE)

( * ) Notice: Subject to any disclaimer, the term of this patent is extended or adjusted under 35 U.S.C. 154(b) by 82 days.

(21) Appl. No.: 13/307,413

(22) Filed: Nov. 30, 2011

(65) Prior Publication Data
US 2012/0257195 A1    Oct. 11, 2012

(30) Foreign Application Priority Data

Apr. 10, 2011 (DE) .......................... 10 2011 017 134

(51) Int. Cl.
*G01N 21/00* (2006.01)
*G01N 21/55* (2006.01)

(52) U.S. Cl.
CPC .............. *G01N 21/00* (2013.01); *G01N 21/55* (2013.01)
USPC ........................................ 356/237.1; 356/445

(58) Field of Classification Search
CPC .............................. G01N 21/00; G01N 21/55
USPC .................... 356/237.1–237.2, 445–448
See application file for complete search history.

(56) References Cited

U.S. PATENT DOCUMENTS

| | | | | |
|---|---|---|---|---|
| 5,353,512 A | * | 10/1994 | Theurer et al. | 33/523.2 |
| 5,386,727 A | * | 2/1995 | Searle | 73/602 |
| 5,893,043 A | * | 4/1999 | Moehlenbrink et al. | 701/446 |

FOREIGN PATENT DOCUMENTS

| | | |
|---|---|---|
| DE | 3210015 | 9/1983 |
| EP | 1548400 | 6/2005 |

* cited by examiner

*Primary Examiner* — Michael P Stafira
(74) *Attorney, Agent, or Firm* — Frommer Lawrence & Haug LLP (57) ABSTRACT

An arrangement for marking and measuring sections of railroad track, which allows track sections which are susceptible to wear to be determined reliably and accurately. A sensor unit is provided for detecting measuring points, and has at least two independent detector units measuring in a non-contacting manner, based on a first optical sensor having spectrally selective sensitivity and a second identification detector. The measuring points, as angle elements, are detachably fastened to the rail and are provided at a horizontally oriented leg with a coating emitting in a narrow spectral band and with an identification value carrier for the identification detector. The sensor unit is so arranged at a device which can travel on tracks that the independent detector units are guided parallel to the rail in the same direction over the measuring points with the movement of the device which can travel on tracks.

14 Claims, 8 Drawing Sheets

ARRANGEMENT FOR MEASURING SECTIONS OF TRACK FOR THE PURPOSE OF MAINTAINING RAILROAD TRACKS

The present application claims priority from German Patent Application Nos. DE 10 2011 017 134.7 filed on Apr. 10, 2011, the disclosure of which is incorporated herein by reference in its entirety.

BACKGROUND OF THE INVENTION

1. Field of the Invention

The invention is directed to an arrangement for marking and measuring sections of track for the purpose of maintaining railroad tracks, particularly in the area of switches, crossovers, curves, and other sections of track that are susceptible to wear.

2. Description of Related Art

Measurements of track for determining maintenance areas are performed in a variety of ways in the art through optical, capacitive, and eddy current measurements. In this connection, automated measurement by measuring trains is usually not sufficiently precise for wear-critical areas to directly control exact work by work machinery (grinding machines or tamping machines). Therefore, there is a need for performing exact in situ measurement of work areas in track maintenance not only in a reliably reproducible manner but also so as to be closely linked to the work machine as far as possible. Computer-assisted measuring apparatuses in current use have so far not been reproducible with sufficient precision—particularly for complicated track areas such as curves or switches—with respect to the position of a work area when a work machine travels over the track area repeatedly and the work must always be resumed exactly at a determined location (determined beforehand by rail profile measuring equipment).

A measuring device which makes it possible to check the state of railroad track in track sections such as curved areas is described in DE 32 10 015 C2. This is a hand-held measuring device for measuring the lateral position and height position of railroad track which uses two reference chords, which are constructed as tripods which can be set up in a stationary manner at a defined distance from one another and have spirit levels, sighting optics and stadia rods, and has a stand base having a crosspiece for deploying on both rails. This measuring device measures the track position over long distances along a large chord of the curve arc and, in order to verify the measurement positions and the track position that is found in this way, further requires reference to fixed points (e.g., overhead line masts) which must be specified by the rail network operator. This does not allow track positions to be freely determined corresponding to the ascertained state of the track for maintenance of the track section.

Another measuring device for inspecting rails, particularly switches, is known from EP 1 548 400 A1. In this case, the rail spacing is detected by a laser distance sensor, an optical waveguide which projects the laser beam on the point to be measured, and a CCD receiver at the location to be measured.

Apart from the fact that the measuring device mentioned above uses optical sensors and, for this reason alone, is not suitable for use in work machinery such as grinding machines, EP 1 548 400 A1 discloses with regard to determining and recognizing the individual measuring points (which can lie at a distance of 2 to 5 mm) that these measuring points are recorded along the distances traveled, which are transmitted to a rotary encoder by the running wheels of the measuring device, and the measuring points are correlated with the measurements taken at the measuring points. This determination of measurement positions is not reproducible with exactitude due to slippage, particularly back-and-forth movements in the curve area, so that the correlation is unsatisfactory for controlling the locations where a work machine is put to use. Further, the rotary encoders present systematic errors which cause an accumulation of errors through wheel slippage during every forward and backward movement in the work area.

While visual detectability is desirable for non-contacting detection of positions, soiling caused by the work machinery impairs position detection of the measuring points so that visual methods cannot be employed in direct combination with work machinery (e.g., rail grinding machines). Consequently, a measuring device for finding measurement locations which have been determined beforehand by rail profile measuring equipment as defective sections of rail or which are defined by rules pertaining to measuring or machining must be designed in such a way that it is capable of reliably and reproducibly collecting position data along the track which cannot be falsified by ambient conditions.

SUMMARY OF THE INVENTION

Therefore, it is the object of the invention to find a novel possibility for marking and measuring sections of track for the purpose of maintaining railroad tracks which allows track sections which are susceptible to wear (e.g., curves and switches) to be determined reliably and accurately with respect to position, also in direct cooperation with work machinery, without requiring for this purpose that rail work be halted for measurement or that working and measurement be disjointed in some other way.

In an arrangement for marking and measuring sections of track for the purpose of maintaining railroad tracks in which means are provided for optical acquisition of measuring points, the above-stated object is met according to the invention in that a sensor unit for detecting measuring points located next to a rail has at least two independent detector units measuring in a non-contacting manner based on different measurement principles, wherein one measurement principle makes use of an optical sensor having spectrally selective sensitivity and a second measurement principle makes use of an identification detector for individual identification of measuring points, in that the measuring points have at least two legs as angle elements, wherein a first, vertically oriented leg is detachably fastened to the rail, and are provided at a second, horizontally oriented leg with a coating emitting in a narrow spectral band for the spectrally selective sensor and with an identification value carrier for the identification detector, and in that the sensor unit is so arranged at a device which can travel on tracks that the independent detector units are guided parallel to the rail in the same direction over the measuring points with the movement of the device which can travel on tracks.

The sensor unit is advantageously constructed so as to be vertically swivelable transverse to the rail.

Further, the sensor unit can usefully be arranged so as to be displaceable transverse to the rail in order to adapt it to rail gauge and orientation of the measuring points with respect to the rail.

A sensor unit for each rail is advantageously provided at the device which can travel on tracks, the sensor units being arranged opposite one another in transverse direction with respect to the track.

The measuring points are advisably detachably fastened to the rail by means of a permanent magnet and are preferably arranged on the outer side or inner side of the web of the rail.

In this connection, it is possible in case of a grooved rail to arrange the measuring points at the guard rail or at the guide rail of a track.

The measuring points are preferably provided with a luminescent layer as a coating which emits in a narrow band. In this variant, the sensor unit advantageously comprises a spectrally selective sensor for luminescent light which is adapted to the emission wavelength range of the luminescent layer.

Second, the measuring points are advisably provided with an identification tag in the form of a RFID chip. For this embodiment, the sensor unit advisably comprises a radio frequency transducer for reading the RFID chip.

In an advantageous manner, the device which can travel on tracks and serves to fasten the sensor unit is a work machine from the group comprising rail grinding machines or rail tamping machines. However, it can also simply be a measuring vehicle.

The invention is premised on the basic consideration that the known rail measuring devices define the determined defective areas either outside of and independently from the stretch of track by way of fixed points (e.g., masts) or require optical detection of fine measuring marks (e.g., barcodes or the like) at the track and determine the position indirectly by means of wheel-driven rotary encoders. In both cases, the customary soiling caused by work performed on the rails (e.g., grinding) impairs optical or mechanical position measurement, although the latter is indispensable for accurately acquiring measurement values.

This problem is solved in the invention through the use of suitable marking elements (hereinafter: measuring points) which are positioned temporarily or for longer periods of time at or in the vicinity of the railroad tracks and whose characteristics are so constituted that they can be detected and acquired with sufficient accuracy actively or passively in a non-contacting manner by a measuring system which is fastened directly to a railborne vehicle.

The invention comprises a combination of specially fabricated measuring points and an accompanying sensor unit having multiple sensitivity.

The entire measuring system for a section of track to be worked on has a plurality of "movable" measuring points which are preferably fastened in a detachable manner directly to a lateral surface of the rail web by means of a permanent magnet. The measuring points are designed in such a way that they can also easily be fastened to the guard rail (check rail) so that they can also be used in closed track (embedded track in street construction).

In so doing, the positions of the measuring points are determined based on the measurement logs of a rail profile measuring device previously employed in the section of track or in conformity with an established rule governing measurement or work, and the measuring points are arranged at the locations which distinguish the starting point and end point of one or more work areas (e.g., for a work machine such as a grinding machine or a tamping machine).

According to the invention, the measuring points are detectable by means of a sensor unit based on at least two qualitatively different measurement principles, the sensor unit being guided along at a device moving on the track. An additional link to and transmission to a GPS is possible by means of simple modifications.

Two non-contact measurement principles are preferably used in conjunction for detection, one of which makes use of an optical principle having the lowest possible susceptibility to faults and using spectrally sensitive marker dyes (based on photoluminescence), while the other measurement principle is one based on radio waves, magnetism or capacitance and allows coding (ID tag). Both principles can operate actively as well as passively, but at least one active principle is advisably used for the ID tag.

With respect to the optical principle, a florescent dye which is sufficiently activated by daylight or by the work lighting of a work machine is preferably detected by a spectrally sensitive optical sensor which is adjusted to the emission wavelengths of the fluorescent dye. In this way, position detection is ensured and confusion or ambiguities in connection with other reflective objects is eliminated.

The measuring point is preferably outfitted with a RFID chip (radio frequency identification chip). This serves to identify the optically detected measuring point and constitutes the "counter" or the classification of the work areas (which can also be "non-work areas") of the section of track to be maintained.

By means of the invention as a combination of two different measurement methods applied to suitably designed measuring points (marking elements), it is possible to implement marking and measurement of sections of track for the purpose of maintaining railroad tracks so as to allow a reliable and positionally accurate determination of sections of track which are susceptible to wear, also in direct cooperation with work machinery, without requiring for this purpose that rail work be halted for measurement or that working and measurement be disjointed in some other way. As a result of the sensor system according to the invention, the position of all of the measuring points and the correct sequence thereof are determined definitively, ambiguities are eliminated, and accuracy of repetition is reproducible over a plurality of passages (exclusion of wheel slippage).

DETAILED DESCRIPTION OF EMBODIMENTS

It is to be understood that the figures and descriptions of the present invention have been simplified to illustrate elements that are relevant for a clear understanding of the present invention, while eliminating, for purposes of clarity, many other elements which are conventional in this art. Those of ordinary skill in the art will recognize that other elements are desirable for implementing the present invention. However, because such elements are well known in the art, and because they do not facilitate a better understanding of the present invention, a discussion of such elements is not provided herein.

The present invention will now be described in detail on the basis of exemplary embodiments.

Figure 1:
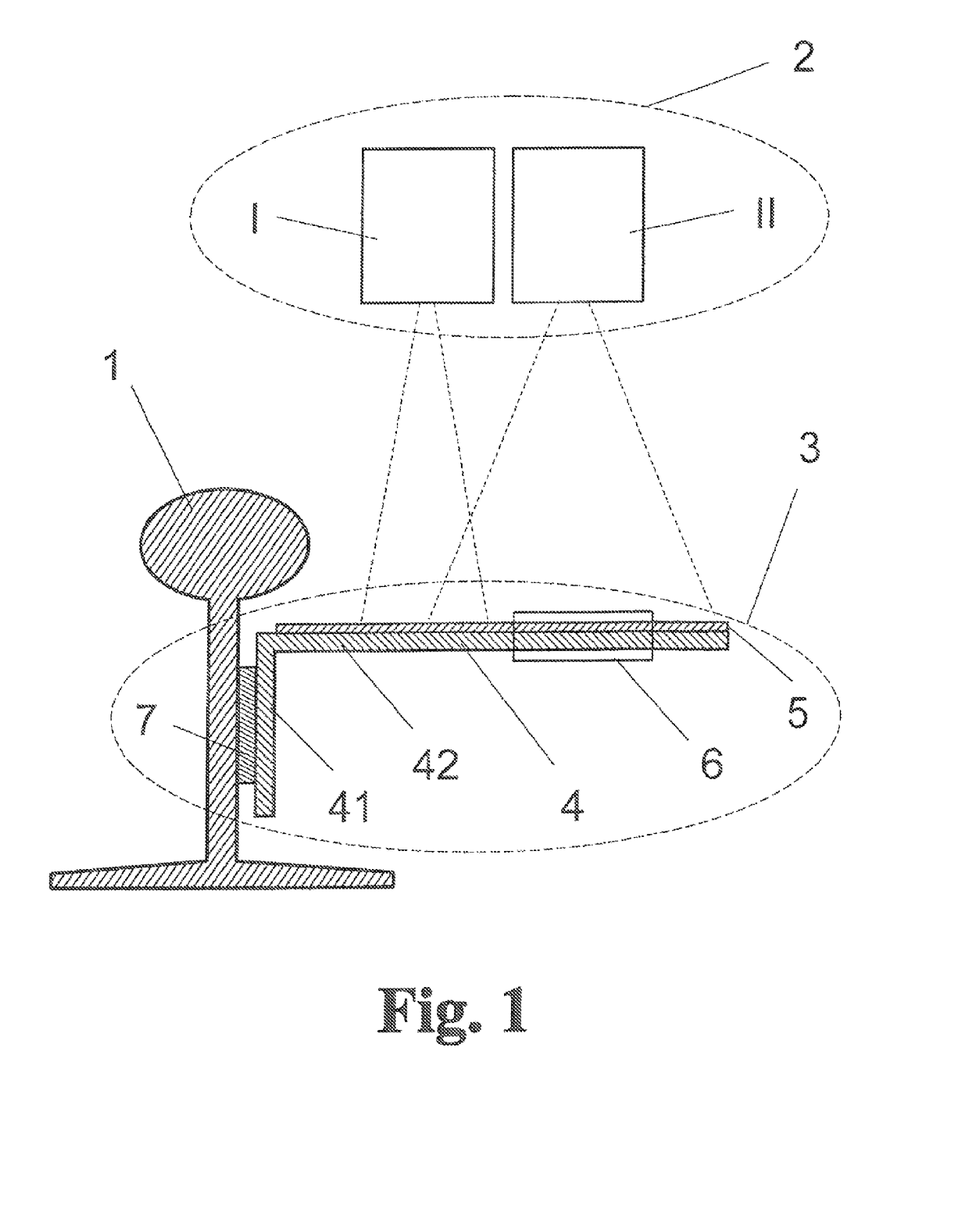
FIG. 1 shows a schematic diagram of a measuring point at a Vignoles rail.

As is shown schematically in FIG. 1, the basic arrangement according to the invention comprises a measuring point 3 which is detachably arranged at a rail 1 (shown in a conventionalized manner as a Vignoles rail). A sensor unit 2 fastened to a work machine 8 is guided over the measuring point 3. The sensor unit 2 comprises two independent detector units which are based on different principles.

The first detector unit is an optical sensor I which can capture spectrally selective radiation within a limited reception range (e.g., having a diameter of 2 cm at a distance of up to 25 cm) and which is adjusted to a radiation emitted by the measuring point 3 in a narrow spectral band.

The second detector unit is designed for a defined ID tag and is preferably an active radio frequency transducer II which can read the programmed value of a RFID chip 6. Its range is designed for approximately 10 to 30 cm and is limited to a transmission/reception cone having approximately the same dimensions.

Figure 5:
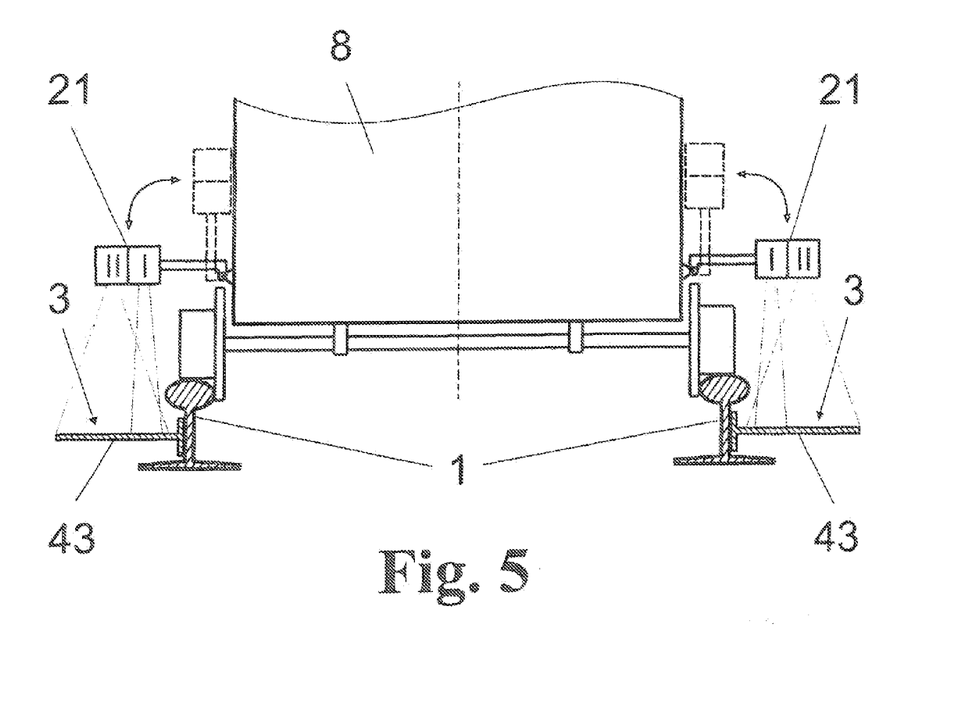
FIG. 5 shows a front view of a work machine with swivelable sensor unit.

The measuring point 3 suited to this sensor unit 2 comprises an angle element 4 (e.g., made of a metal such as steel, stainless steel, brass, or the like, a stable plastic or composite such as CRP, GRP, ARP, or SRP, or other durable, dimensionally stable materials). The angle element 4 has at least two legs, a permanent magnet 7 being fastened to or recessed into a shorter 41 of the two legs, and a luminescent layer 5 (preferably of fluorescent or phosphorescent material) being arranged on the upper side of a longer leg 42. The outer side of the long leg 42 is directed upward toward the sensor unit 2. Further, the RFID chip 6 which contains the ID tag and can be read out by the radio frequency transducer II is arranged at the long leg 42 of the angle element 4. In specific embodiments, short legs 41 can branch off from both sides of the long leg 41 resulting in a T-shaped angle element 43 (as is shown in FIG. 5).

While the optical sensor I detects a very narrow reception range (of about 6 to 8 cm), preferably for detection of a fluorescent dye, as luminescent layer 5, which is sufficiently activated by daylight or by the work lighting of the work machine 8 and therefore ensures sufficient position detection, the radio frequency transducer II is responsible for identifying the measuring point 3 and is, therefore, a detector within the meaning of a "counter" or a classifier for interpreting the work area for the work machine 8, which work area follows the measuring point 3. For this purpose, every measuring point 3 is outfitted with a RFID chip 6 in which a determined ID value is programmed.

The simplest "counter" code consists in the alternating allocation of an 0/L code of the measuring points 3, where "0" identifies the start position and "L" identifies the end position for the individual work areas of the work machine 8.

In case the section of track which is to be maintained and in which the work machine 8 (repeatedly) travels back and forth over the section of track performing work has a plurality of work areas (and, therefore, a plurality of measuring points 3) or areas comprising different work steps, divergent or expanded digital identifiers can be programmed in the RFID chip 6 for producing the unambiguous assignment of measuring points 3.

The measuring point 3 is preferably detected passively and actively by the sensor unit 2 which is moved over the section of track with the work machine 8. Two non-contact measuring methods are employed jointly during detection so that an optical principle having the lowest possible susceptibility to faults and using a coating (luminescent layer 5) which emits in a narrow spectral band for accurately determining the position in the track is combined with a radio frequency transducer II which ascertains the uniquely determined purpose of the measuring point 3 and at the same time excludes the possibility that an extraneous signal detected by the optical sensor I can be further processed erroneously as a measuring point 3.

Alternatively, magnetic or capacitive measurement principles can also be used for detecting an ID tag.

Accordingly, as a result of the sensor system according to the invention, the position of all of the measuring points 3 and the correct sequence thereof are determined definitively, ambiguities are eliminated, and repetitive accuracy of measurement point detection is reproducible over a plurality of passages (exclusion of erroneous positions due to wheel slippage).

The measuring points 3 can be used for different track markings, arranged and rearranged as necessary, reused as often as required and displaced if required so that they can be used for alterations and expansions (repair work) at the work sites or repeatedly between the latter and always in a unambiguously assignable manner.

The florescent coating (luminescent layer 5) can be restored directly on-site at the construction site in case of surface damage (soiling, mechanical influences) in a simple manner (e.g., by means of fluorescent spray paint). Therefore, the measuring points 3 are resistant to wear provided that the RFID chip 6 is nor damaged, and the signals of the measuring points 3 are reproducible provided that the measuring points 3 are not accidentally displaced along the rail 1.

The measuring points 3 are preferably produced as angle elements 4 having a width of 2 to 8 cm (preferably 4 cm) and have leg lengths between 2 and 6 cm (preferably 3 cm) for the short leg 41 and 10 to 20 cm (preferably 12 to 15 cm) for the long leg 42. In this connection, the short leg 41 can also be entirely or partially replaced by the permanent magnet 7, or two short legs 41 can branch off from both sides of the long leg 42 resulting in a T-shape.

For the spatial resolution of the position of the measuring points 3, a positioning accuracy of 1 cm can be maintained without difficulty—even when the width of the angle element 4 is several centimeters—because it can be determined easily and accurately by center detection or edge detection in the captured optical image of the measuring point 3.

Since visual recognition (high-resolution point detection) is unnecessary, normal soiling does not impair position detection of the measuring points 3 by the optical sensor I. However, in order to limit work soiling (e.g., grinding dust), air currents can be introduced additionally, preferably by means of nozzles (not shown), in the measuring gap between the measuring point 3 and sensor unit 2. The measuring gap is between 10 cm and 30 cm, optimally around 15 cm, in the aforementioned detection units (optical sensor I and radio frequency transducer II).

Figure 6:
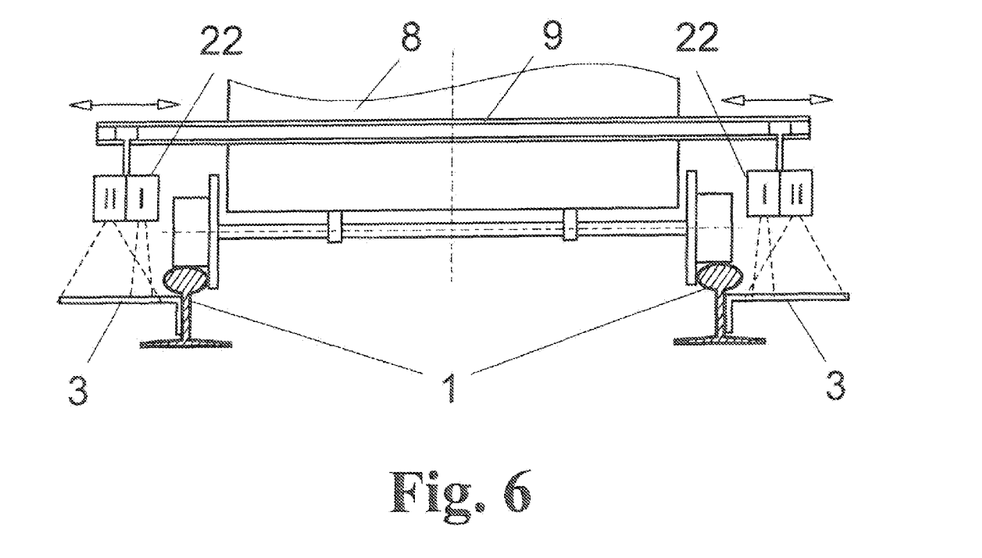
FIG. 6 shows a front view of a work machine with displaceable sensor unit, fastening on the outside (Vignoles rail)
Figure 7:
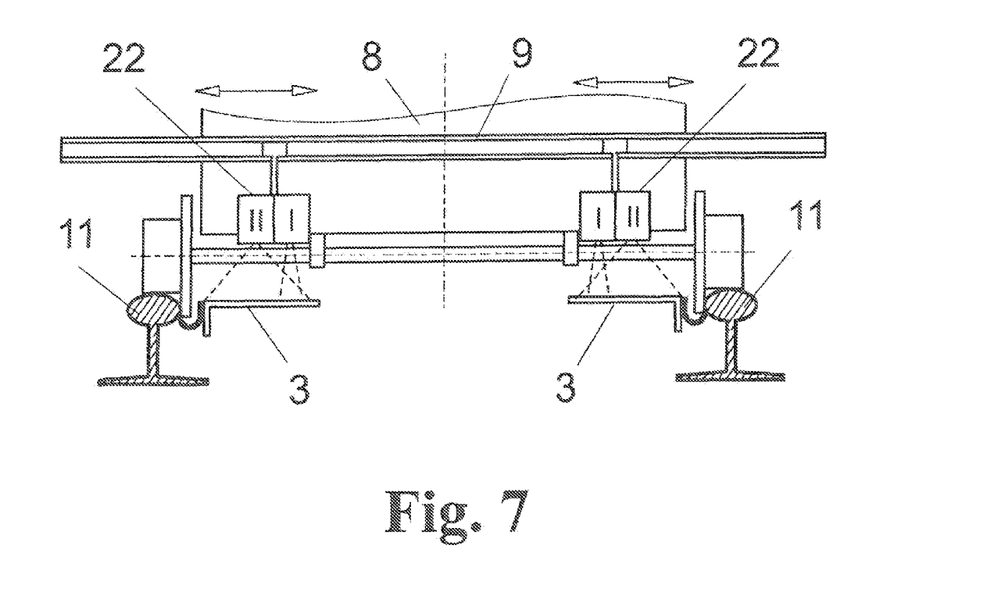
FIG. 7 shows a front view of a work machine with displaceable sensor unit, fastening on the inside (grooved rail)
Figure 8:
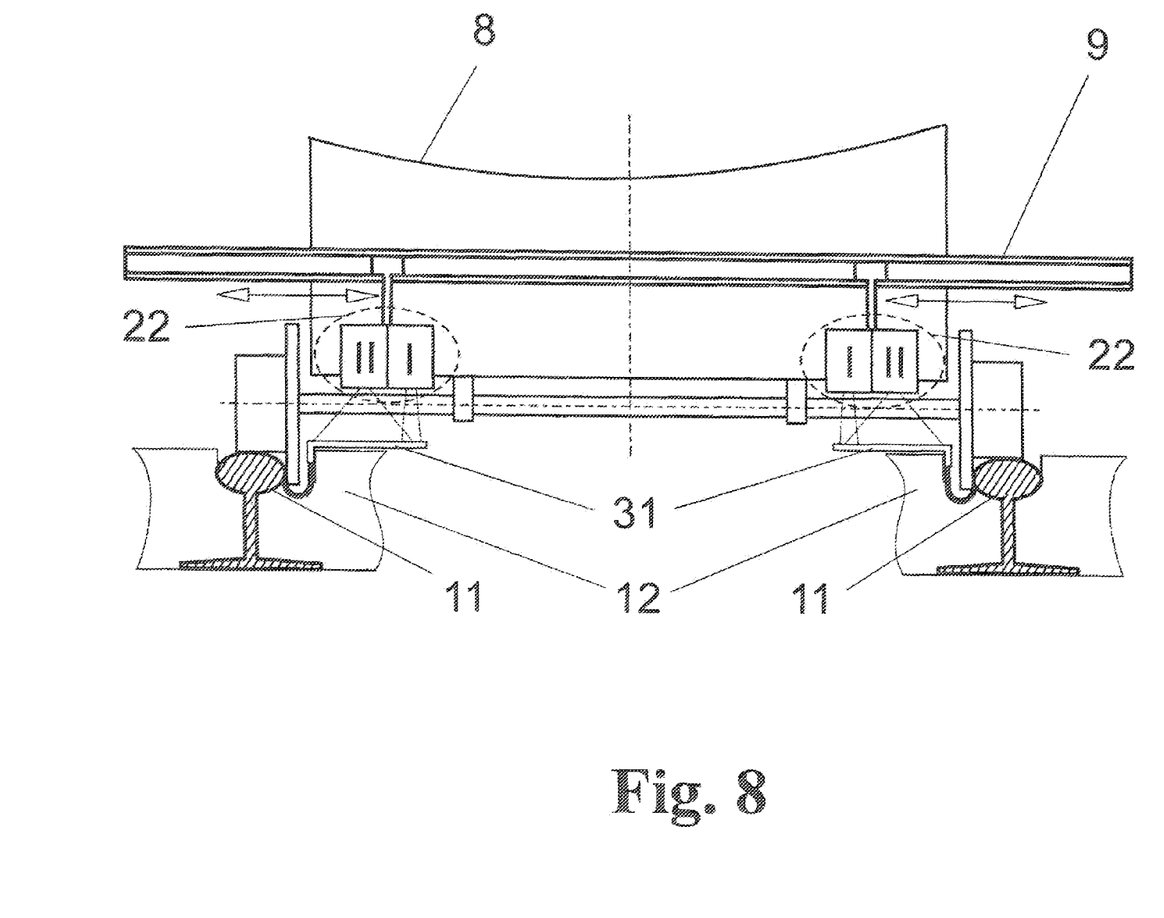
FIG. 8 shows a front view of a work machine with displaceable sensor unit, fastening on the inside (on the grooved rail)

The entire measuring system for a section of track to be worked on has a plurality of "movable" measuring points 3 which are fastened temporarily to or in the vicinity of the railroad tracks 1 in a simple manner; fastening is reliably carried out by means of a permanent magnet 7 directly at a side surface of the respective rail 1. In order to be able to use the measuring points 3 also in closed track construction (embedded track), they are designed in such a way that they can also be fastened to the guard rail (check rail) without difficulty. Fastening is preferably carried out at the outer side of the track as is shown in FIGS. 5 and 6. However, there is a wide variety of special track sections which require arrangement at the inner side of the track or also at a guard rail (check rail) or a guide rail as is shown in FIGS. 7 and 8.

The management of an arrangement of the type described above is shown in FIGS. 2 and 3. For the sake of clarity, only the different measuring points 3 in the track area of a switch are shown.

Before the track is worked on by the work machine 8, defined work areas are determined in certain sections of track based on previously determined rail wear conditions or on prescribed work tasks, and the measuring points 3 are positioned in a corresponding manner. The positions are read in by means of the sensor unit 2, and the data is processed, stored and made available for the automatic control of the work machine 8.

Figure 2:
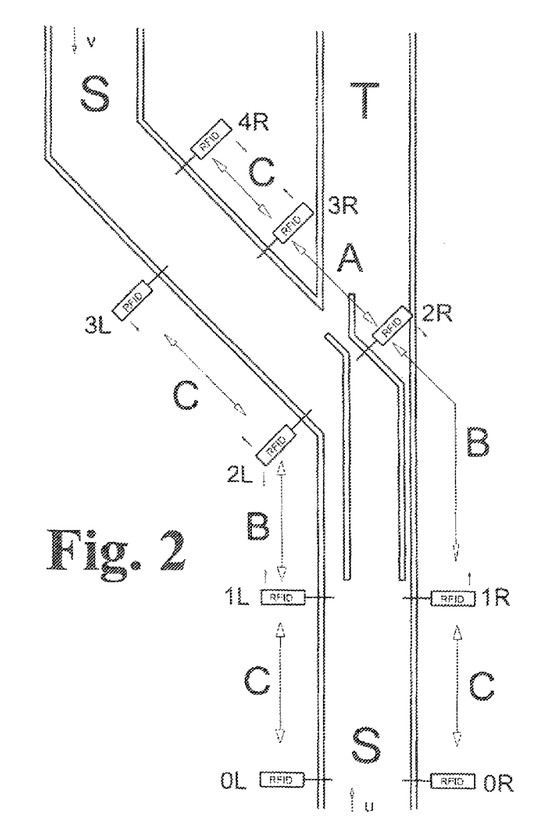
FIG. 2 shows an arrangement of the measuring points in the area of a switch (with crossover)

FIG. 2 shows different work areas during track maintenance in a section of track having a switch which is set to cross over to the left (section turning S). In this case, measuring point positions 0L to 1L, 1L to 2L, and 2L to 3L are to be detected at the left-hand rail 1 as work areas B and C, while sections 0R to 1R, 1R to 2R, and 3R to 4R at the right-hand rail 1 are work areas and section 2R to 3R at the right-hand rail 1 is an area A without work.

The individual work areas of the section of track shown in the drawing can be specified as follows:
  A—area without work (through-travel only)
  B—area with restricted work (switch section)
  C—area with complete work on the rail surface (grinding of a complete section).

Figure 3:
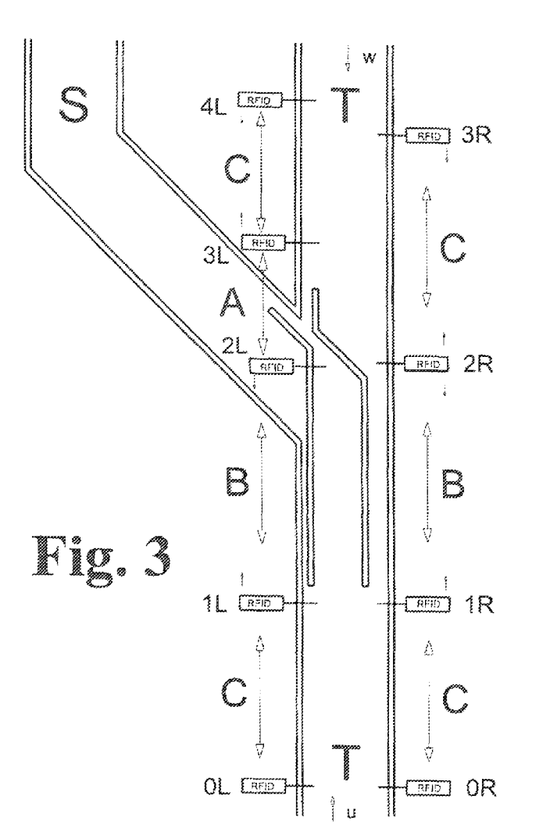
FIG. 3 shows an arrangement of the measuring points in the area of a switch (no crossover)

In FIG. 3, the route with straight travel T (no crossover) is adjusted by the switch. This results in areas 0L to 1L, 1L to 2L, and 3L to 4L as active work areas which are areas with restricted work B or areas with complete work C. On the right-hand rail 1, the head of the rail 1 is to be worked upon only partially (area B with restricted work) in the area of the switch in section L1 to L2, while work is suspended between 2L and 3L in an (passive) area A without work (i.e., the grinding elements (not shown) of the work machine 8 are at a safe distance from the rail 1 so that the switch is not damaged). In measuring point position 3L, the work resumes and is carried out until position 4L. On the right-hand rail 1, the rail head is completely reworked in the sections from 0R to 1R and 2R to 3R, while it is only partially worked between measuring positions 1R and 2R.

This manner of work can be repeated as often as required for each rail 1; it does not matter whether the work machine 8 with the sensor unit 2 travels over the area forward or backward, since the measuring points 3 guarantee an unambiguous assignment of position and area.

This method of point-exact control' of the work machine 8 can be applied in any section of track, particularly also inside switches. In so doing, danger spots (i.e., locations which may not be damaged) are marked and a flawless working of the rail 1 is carried out in that the sensor unit 2 detects the position exactly. The exact and unmistakable detection of measuring points 3 also allows work to be carried out on a plurality of successive switches of any shape.

Figure 4:
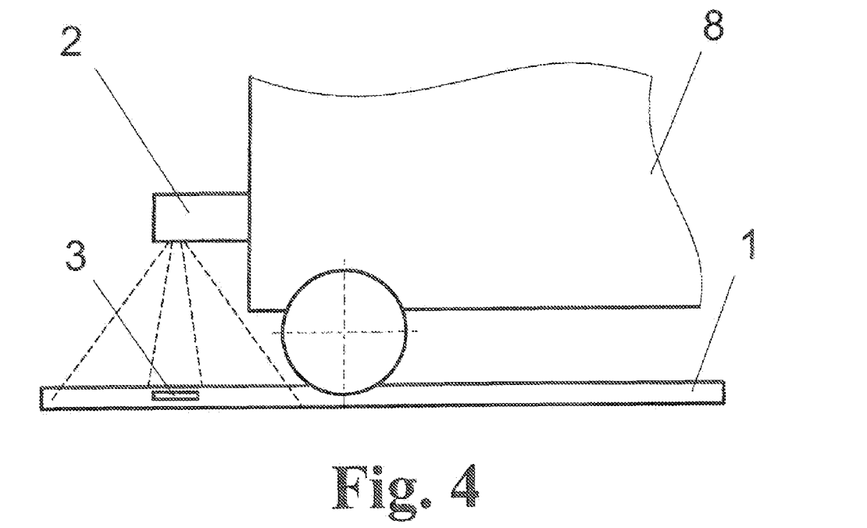
FIG. 4 shows a side view of a work machine with fastening of the sensor unit in the mat.

In a side view of the work machine 8, FIG. 4 shows that the sensor unit 2 is arranged in the front or rear area of the work machine 8. A view of a front/rear area of the work machine 8, correspondingly offset by 90° in FIG. 5, shows that when measuring points 3 are arranged on the outer side of the track the detector units I and II (optical sensor I and radio frequency transducer II) are advantageously constructed as swivelable sensor unit 21 so as to keep the latter safely away from the measuring and working operations of the work machine 8, preferably in a housing niche (not shown) (e.g., when the work machine 8 is moved from one construction site to the next).

Further, FIG. 5 shows another preferred embodiment form of the measuring points 3 in which T-shaped angle elements 43 are fitted to the outer side of the web of the rail 1. In so doing, the short legs 41 fitted to the web can also be formed by the permanent magnet 7 in that the long leg 42 is glued directly to the permanent magnet 7.

FIGS. 6 and 7 show a preferred embodiment of the invention in which the detector units I and II are constructed as sensor unit 22 which is displaceable transverse to the track direction. FIG. 6 shows the position of the displaceable sensor unit 22 moved out along a crosspiece 9 for detecting measuring points 3 arranged on the outer side of the rails 1, while FIG. 7 shows the moved in position for measuring points 3 fastened to the inner side at a groove rail 11. In the latter fastening, the guard rail (check rail) is used for arranging the measuring point 3 by means of the magnet 7 (not shown here for the sake of simplicity).

FIG. 8 shows a similar situation in which a section of track in embedded construction makes an arrangement of the measuring points 3 at the guard rail (check rail) of the grooved rail 11 mandatory, since no other fastening possibilities are available. Because of the confined space conditions commonly found next to the grooved rail 11, it is sometimes necessary to adapt the shape of the measuring point 3.

Figure 9:
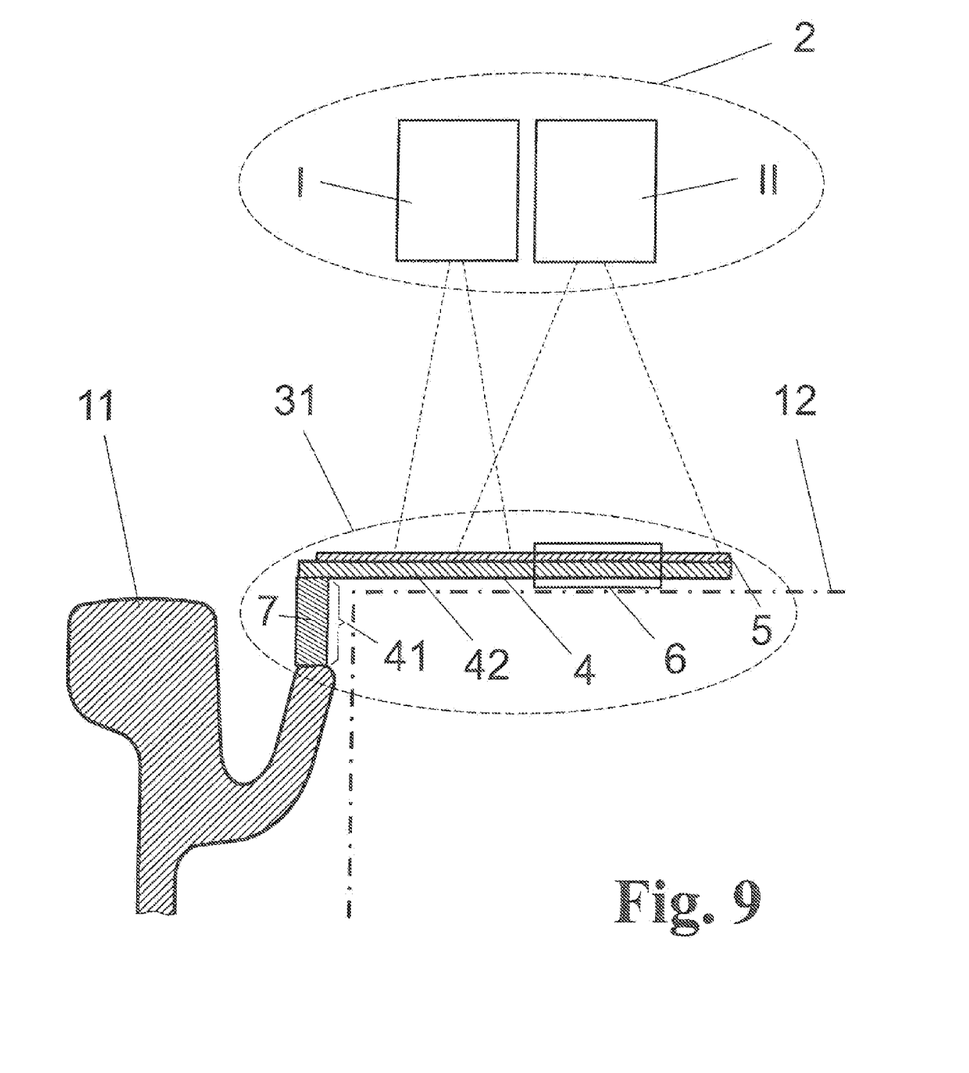
FIG. 9 shows a schematic diagram of a measuring point with a grooved rail in the encasement area having a magnet which is constructed as the shorter leg of the angle element for fastening the measuring point.

This type of modification of the measuring point 3 is shown in the enlarged view in FIG. 9. In this case, the measuring point 3 is modified in such a way that it preferably lies directly on the road support construction (encasement area 12) and is fixed by frictional engagement at the guard rail of the grooved rail 11 by the permanent magnet 7.

Figure 10:
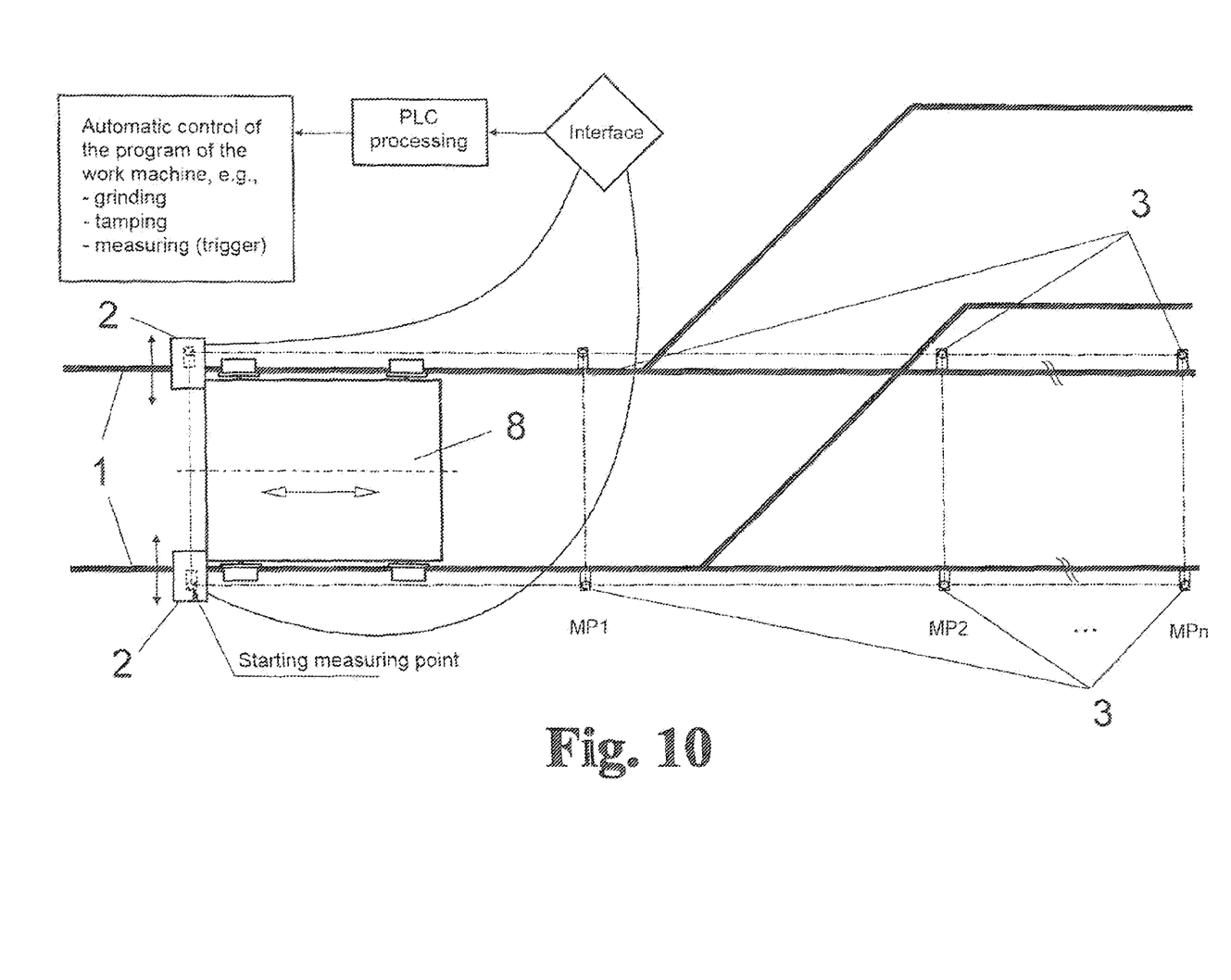
FIG. 10 shows an illustration of the principle of operation of measuring point detection for the direct control of the work machine based on the acquired measuring points.
Figure 11:
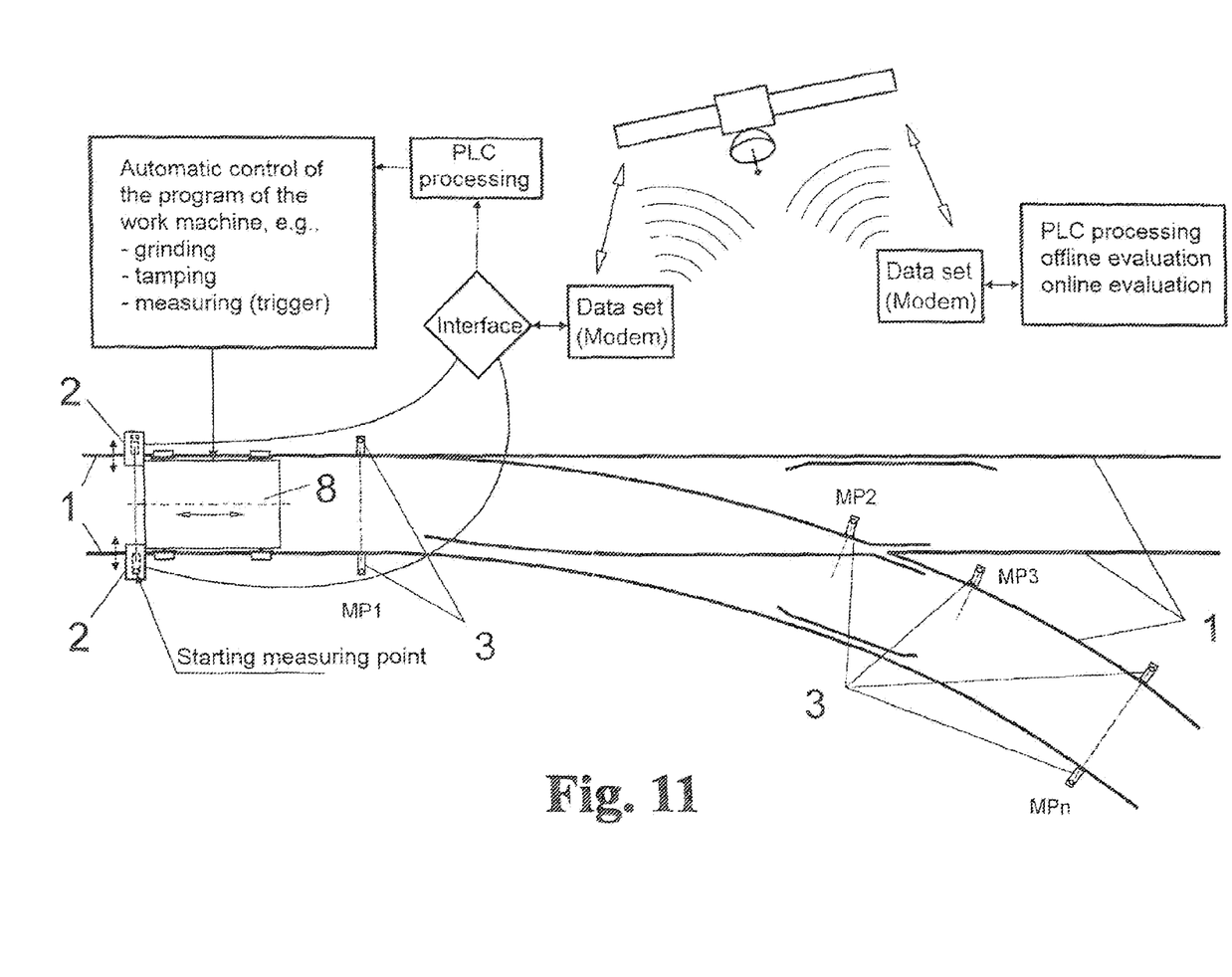
FIG. 11 shows an illustration of the principle of operation of measuring point detection for data acquisition and data processing of work machines using GPS.

FIGS. 10 and 11 show a schematic diagram of the operating mode of detection of measuring points 3 as a data transfer schema for direct control of the work machine 8 and for the integration of the acquired data using a GPS. The signals acquired from the measuring points 3 by means of the sensor units 2 are sent in a suitable manner via an interface to a computer unit (PLC) in which they are further processed in order to carry out specific work steps directly in the work machine 8. In FIG. 11, in which the acquisition of measurement data is the same, a modem is connected downstream of the PLC so that the data (coordinates of the measuring points 3 and measured values) is supplied in a retrievable manner via satellite to other locations around the world (in a suitable manner via the Internet to a remote station having the corresponding access data).

While this invention has been described in conjunction with the specific embodiments outlined above, it is evident that many alternatives, modifications, and variations will be apparent to those skilled in the art. Accordingly, the preferred embodiments of the invention as set forth above are intended to be illustrative, not limiting. Various changes may be made without departing from the spirit and scope of the inventions as defined in the following claims.

REFERENCE NUMERALS 1 rail (conventionalized Vignoles rail)
11 grooved rail 12 encasement area
2 sensor unit
21 swivelable sensor unit
22 displaceable sensor unit
I optical sensor
II radio frequency transducer
3 measuring point
31 measuring point for encasement area
4 angle element
41 short leg
42 long leg
43 T-shaped angle element
5 luminescent layer
6 RFID chip
7 permanent magnet
8 work machine
9 crosspiece (for displacing the sensor unit)
A area without work (non-work area)
B area with restricted work (on the rail head)
C area with complete work (on the rail head)
S section with turn-off
T straight section
u, v, w travel direction

What is claimed is:

1. An arrangement for marking and measuring sections of track for the purpose of maintaining railroad tracks, comprising:
  means for optical detection of measuring points; and
  a sensor unit for detecting measuring points which is configured to be located next to a rail, the sensor unit including:
    an optical sensor having spectrally selective sensitivity, where the optical sensor measures in a non-contact manner; and
    an identification detector for individual identification of measuring points, where the identification detector measures in a non-contact manner;
  wherein the measuring points include at least a first, vertically oriented leg and a second, horizontally oriented leg as angle elements;
  wherein the first, vertically oriented leg is configured to be detachably fastened to the rail;
  wherein the second, horizontally oriented leg has a coating which emits in a narrow spectral band for the spectrally selective sensor, and has an identification value carrier for the identification detector;
  wherein the sensor unit is arranged at a device configured to travel on tracks, so that the optical sensor and the identification detector are configured to be guided parallel to the rail in a same direction over the measuring points with a movement of the device.

2. An arrangement according to claim 1;
wherein the sensor unit is configured to be swivelable vertically transverse to the rail.

3. The arrangement according to claim 1;
wherein the sensor unit is arranged so as to be displaceable transverse to the rail in order to adapt the sensor unit to rail gauge and orientation of the measuring points with respect to the rail.

4. The arrangement according to claim 1;
wherein a sensor unit for each rail is provided at the device which can travel on tracks, so that the sensor units are arranged opposite one another in a transverse direction with respect to the track.

5. The arrangement according to claim 1;
wherein the measuring points arc configured to be detachably fastened to the rail by means of a permanent magnet.

6. The arrangement according to claim 5;
wherein the measuring points arc arranged at a web of the rail.

7. The arrangement according to claim 1;
wherein the measuring points are arranged at a guard rail of a grooved rail.

8. The arrangement according to claim 5;
wherein the measuring points are arranged at a guide rail of the track.

9. The arrangement according to claim 1;
wherein the measuring points are provided with a luminescent layer as a coating which emits in a narrow band.

10. The arrangement according to claim 9;
the sensor unit comprises a spectrally selective sensor for luminescent light which is adapted to the emission wavelength range of the luminescent layer.

11. The arrangement according to claim 1;
wherein the measuring points wherein are provided with an RFID chip as an identification value carrier.

12. The arrangement according to claim 11;
wherein the sensor unit comprises a radio frequency transducer for reading the RFID chip.

13. The arrangement according to claim 1;
wherein the device which can travel on tracks is a work machine selected from a group consisting of rail grinding machines and tamping machines.

14. The arrangement according to claim 13;
wherein the device which can travel on tracks is a measuring vehicle.

* * * * *